United States Patent
Afzali-Ardakani et al.

(10) Patent No.: US 10,029,915 B2
(45) Date of Patent: Jul. 24, 2018

(54) FUNCTIONALLY SWITCHABLE SELF-ASSEMBLED COATING COMPOUND FOR CONTROLLING TRANSLOCATION OF MOLECULE THROUGH NANOPORES

(75) Inventors: Ali Afzali-Ardakani, Ossinging, NY (US); Stefan Harrer, Hampton (DE); Binquan Luan, Pleasantville, NY (US); Hongbo Peng, Chappaqua, NY (US); Gustavo A. Stolovitzky, Riverdale, NY (US); Deqiang Wang, Ossining, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 1182 days.

(21) Appl. No.: 13/439,265

(22) Filed: Apr. 4, 2012

(65) Prior Publication Data

US 2013/0263946 A1    Oct. 10, 2013

(51) Int. Cl.
| | |
|---|---|
| *G01N 27/40* | (2006.01) |
| *B82Y 30/00* | (2011.01) |
| *B82Y 40/00* | (2011.01) |
| *F03B 11/02* | (2006.01) |

(Continued)

(52) U.S. Cl.
CPC ............. *B82Y 15/00* (2013.01); *B82Y 30/00* (2013.01); *B82Y 40/00* (2013.01); *G01N 27/00* (2013.01); *Y10T 137/8593* (2015.04)

(58) Field of Classification Search
CPC .. B82Y 15/00; Y02E 10/226; Y10T 137/8593
See application file for complete search history.

(56) References Cited

U.S. PATENT DOCUMENTS

| | | |
|---|---|---|
| 4,450,428 A | 5/1984 | Ohta et al. |
| 4,576,829 A | 3/1986 | Kaganowicz et al. |
| 4,692,992 A | 9/1987 | Hsu |

(Continued)

FOREIGN PATENT DOCUMENTS

| | | |
|---|---|---|
| EP | 0261592 A1 | 9/1987 |
| EP | 1441213 | 7/2004 |

(Continued)

OTHER PUBLICATIONS

Yamaguchi et al., Nature Materials, at www.nature.com/naturematerials, vol. 3, May 2004, 5 pages.*

(Continued)

*Primary Examiner* — Bobby Ramdhanie
*Assistant Examiner* — Denise R Anderson
(74) *Attorney, Agent, or Firm* — Cantor Colburn LLP; Vazken Alexanian

(57) ABSTRACT

A technique for a nanodevice is provided. The nanodevice includes a fluidic cell, and a membrane dividing the fluidic cell. A nanopore is formed through the membrane, and the nanopore is coated with an organic compound. A first part of the organic compound binds to a surface of the nanopore and a second part of the organic compound is exposed freely inside of the nanopore. The second part of the organic compound is configured to be switched among a first neutral hydrophilic end group, a second negatively charged hydrophilic end group, and a third neutral hydrophobic end group based on a switching mechanism.

10 Claims, 9 Drawing Sheets

(51) Int. Cl.
 *B82Y 15/00* (2011.01)
 *G01N 27/00* (2006.01)

(56) References Cited

U.S. PATENT DOCUMENTS

| | | |
|---|---|---|
| 5,671,086 A | 9/1997 | Parvin et al. |
| 5,849,165 A | 12/1998 | Kojima et al. |
| 6,180,490 B1 | 1/2001 | Vassiliev et al. |
| 6,217,872 B1 | 4/2001 | Okayama et al. |
| 6,413,792 B1 | 7/2002 | Sauer et al. |
| 6,582,926 B1 | 6/2003 | Chilkoti |
| 6,621,191 B1 | 9/2003 | Nomura et al. |
| 6,627,067 B1 | 9/2003 | Branton et al. |
| 6,727,174 B1 | 4/2004 | Kotecki et al. |
| 6,777,260 B1 | 8/2004 | Chen |
| 6,783,643 B2 | 8/2004 | Golovchenko et al. |
| 6,862,919 B2 | 3/2005 | Lin et al. |
| 6,962,849 B1 | 11/2005 | Kamal et al. |
| 7,282,130 B2 | 10/2007 | Flory |
| 7,347,921 B2 | 3/2008 | Barth et al. |
| 7,351,648 B2 | 4/2008 | Furukawa et al. |
| 7,410,564 B2 | 8/2008 | Flory |
| 7,468,271 B2 | 12/2008 | Golovchenko et al. |
| 7,540,717 B2 | 6/2009 | Sheng et al. |
| 7,553,730 B2 | 6/2009 | Barth et al. |
| 7,560,141 B1 | 7/2009 | Kim et al. |
| 7,582,490 B2 | 9/2009 | Golovchenko et al. |
| 7,846,738 B2 | 12/2010 | Golovchenko et al. |
| 8,354,336 B2 | 1/2013 | Afzali-Ardakani et al. |
| 8,702,948 B2 | 4/2014 | Ronaghi et al. |
| 8,852,407 B2 | 10/2014 | Peng et al. |
| 8,986,524 B2 | 3/2015 | Afzali-Ardakani et al. |
| 9,121,843 B2 | 9/2015 | Meller et al. |
| 2004/0180369 A1* | 9/2004 | Franzen et al. ............... 435/6 |
| 2004/0229386 A1 | 11/2004 | Golovchenko et al. |
| 2004/0265571 A1* | 12/2004 | Schwartz ............... B05D 1/185 |
| | | 428/333 |
| 2005/0019784 A1 | 1/2005 | Su et al. |
| 2005/0026238 A1 | 2/2005 | Berndt |
| 2005/0101100 A1 | 5/2005 | Kretchmer et al. |
| 2005/0102721 A1 | 5/2005 | Barth |
| 2005/0110990 A1 | 5/2005 | Koo et al. |
| 2005/0158763 A1 | 7/2005 | Ivanisevic et al. |
| 2005/0202446 A1 | 9/2005 | Yang et al. |
| 2006/0015440 A1 | 1/2006 | Penney |
| 2006/0105553 A1 | 5/2006 | Wellhausen |
| 2006/0144824 A1* | 7/2006 | Carter ............... C03C 19/00 |
| | | 216/89 |
| 2006/0154399 A1 | 7/2006 | Sauer et al. |
| 2006/0169588 A1 | 8/2006 | Jacobson et al. |
| 2006/0180469 A1 | 8/2006 | Han et al. |
| 2006/0246497 A1 | 11/2006 | Huang et al. |
| 2006/0275778 A1 | 12/2006 | Wu et al. |
| 2007/0020146 A1 | 1/2007 | Young et al. |
| 2007/0042366 A1* | 2/2007 | Ling ............... 435/6 |
| 2007/0048745 A1 | 3/2007 | Joyce et al. |
| 2007/0138132 A1 | 6/2007 | Barth |
| 2007/0187694 A1 | 8/2007 | Pfeiffer |
| 2007/0190542 A1 | 8/2007 | Ling et al. |
| 2008/0003571 A1 | 1/2008 | McKernan et al. |
| 2008/0032290 A1 | 2/2008 | Young |
| 2008/0102504 A1 | 5/2008 | Akeson et al. |
| 2008/0105539 A1 | 5/2008 | Lyding et al. |
| 2008/0119366 A1 | 5/2008 | Sauer et al. |
| 2008/0171316 A1 | 7/2008 | Golovchenko et al. |
| 2008/0187915 A1 | 8/2008 | Polonsky et al. |
| 2008/0257859 A1 | 10/2008 | Golovchenko et al. |
| 2009/0136958 A1 | 5/2009 | Gershow et al. |
| 2009/0188794 A1 | 7/2009 | Simon et al. |
| 2009/0221443 A1 | 9/2009 | Heller et al. |
| 2009/0222216 A1 | 9/2009 | Hibbs et al. |
| 2009/0232724 A1* | 9/2009 | Afzali-Ardakani et al. ............... 423/447.2 |
| 2009/0295372 A1 | 12/2009 | Krstic et al. |
| 2009/0312197 A1* | 12/2009 | Lee ............... C07K 14/003 |
| | | 506/17 |
| 2010/0025249 A1 | 2/2010 | Polonsky et al. |
| 2010/0025263 A1 | 2/2010 | White et al. |
| 2010/0084276 A1 | 4/2010 | Lindsay |
| 2010/0219339 A1 | 9/2010 | Ogawa et al. |
| 2010/0252434 A1 | 10/2010 | Roy |
| 2010/0327255 A1 | 12/2010 | Peng et al. |
| 2010/0327847 A1 | 12/2010 | Leiber et al. |
| 2010/0331194 A1 | 12/2010 | Turner et al. |
| 2011/0052813 A1 | 3/2011 | Ho et al. |
| 2011/0085759 A1 | 4/2011 | Lee et al. |
| 2011/0120868 A1 | 5/2011 | Lindsay et al. |
| 2011/0174629 A1 | 7/2011 | Bouchet et al. |
| 2011/0220574 A1 | 9/2011 | Olgica et al. |
| 2011/0236984 A1 | 9/2011 | Sun et al. |
| 2011/0279125 A1 | 11/2011 | Bedell et al. |
| 2012/0037919 A1 | 2/2012 | Xu et al. |
| 2012/0076710 A1 | 3/2012 | Waller et al. |
| 2012/0100627 A1 | 4/2012 | Bekki et al. |
| 2012/0146162 A1 | 6/2012 | Cho et al. |
| 2012/0160708 A1 | 6/2012 | Kohli et al. |
| 2012/0193231 A1 | 8/2012 | Afzali-Ardakani et al. |
| 2012/0193235 A1 | 8/2012 | Afzali-Ardakani et al. |
| 2012/0193236 A1 | 8/2012 | Peng et al. |
| 2012/0193237 A1 | 8/2012 | Afzali-Ardakani et al. |
| 2012/0234679 A1 | 9/2012 | Garaj et al. |
| 2012/0306018 A1 | 12/2012 | Gates et al. |
| 2012/0325664 A1 | 12/2012 | Shim et al. |
| 2013/0037410 A1 | 2/2013 | Xu et al. |
| 2013/0062212 A1* | 3/2013 | Afzali-Ardakani .... C25D 5/028 |
| | | 205/114 |
| 2013/0082233 A1 | 4/2013 | Afzali-Ardakani et al. |
| 2013/0203050 A1 | 8/2013 | Huber et al. |
| 2013/0265031 A1 | 10/2013 | Shim et al. |
| 2014/0171774 A1 | 6/2014 | Spira et al. |
| 2015/0160159 A1 | 6/2015 | Afzali-Ardakani |

FOREIGN PATENT DOCUMENTS

| | | |
|---|---|---|
| EP | 1486775 A | 12/2004 |
| KR | 100915061 B1 | 9/2009 |
| WO | WO0181908 A | 11/2001 |
| WO | WO2006122317 | 11/2006 |
| WO | WO2007084163 A | 7/2007 |
| WO | WO2008051308 A2 | 5/2008 |
| WO | WO2008132643 A1 | 11/2008 |
| WO | WO2009020682 A2 | 2/2009 |
| WO | WO2009032756 A2 | 3/2009 |
| WO | WO 2009/117522 A2 * | 9/2009 ............. B82Y 15/00 |

OTHER PUBLICATIONS

Dubey et al., Langmuir, Sep. 21, 2010; 26(18): 14747-14754, 24 pages.*
Oxford Dictionary, "The Concise Oxford Dictionary," 10th ed., ed. Judy Pearsall, pub. Oxford University Press, NY, 1999, 5 pages.*
Solomons et al., "Organic Chemistry," 8th ed., pub. John Wiley & Sons, Inc., Hoboken, NJ, 2004, 5 pages.*
Hu et al., Langmuir, 1997, 12, 5114-5119, 6 pages.*
Free University of Berlin, Jun. 10, 2007, accessed on the Internet at https://web.archive.org/web/20070601000000*/http://userpage.chemie.fu-berlin.de/~tlehmann/krebs/files_diazoalkanes.pdf on Jul. 2, 2015, 31 pages.*
Oxford Dictionary, "The Concise Oxford Dictionary," 10th ed., ed. Judy Pearsall, pub. Oxford University Press, New York, 1999, 3 pages.*
Fologea et al., Electrophoresis 28(18) (2007) 3186-3192, 14 pages.*
Iqbal et al., Nature Nanotechnology 2 (2007) 243-248, 6 pages.*
Schneider et al., Nano Letters 10 (2010) 3163-3167, 5 pages.*
Aksimentiev et al., Biophysical J. 87 (2004) 2086-2097, 12 pages.*
Heng et al., Biophysical J. 90 (2006) 1098-1106, 9 pages.*
Kox et al., Nanotechnology 21 (2010) 1-7, 7 pages.*
Powell et al., Nature Nanotechnology 6 (2011) 798-802, 5 pages.*
Harrer et al., Nanotechnology 22 (2011) 1-6, 6 pages.*
Meller et al., Proc. Nat'l. Acad. Sci. USA 97 (2000) 1079-1084, 6 pages.*

(56) References Cited

OTHER PUBLICATIONS

Raider et al., J. Electrochem. Soc.: Solid-State Sci. & Tech. 123 (1976) 560-565, 6 pages.*
U.S. Appl. No. 13/439,265, dated Sep. 21, 2017, 9 pages. (Year: 2017).*
He, et al., "Identification of DNA Basepairing via Tunnel-Current Decay," Nano Letters 2007; vol. 7, No. 12; pp. 3854-3858.
G. Sigalov, et al., "Detection of DNA Sequences Using an Alternating Electric Field in a Nanopore Capacitor," Nano Letters 2008, vol. 8, No. 1; pp. 56-63.
H. Stranneheim, et al., "Stepping Stones in DNA Sequencing," Biotechnical Journal (2012) 7 (9) pp. 1063-1073.
D. Branton et al., "The Potential and Challenges of DNA Sequencing," Nat. Biotech., vol. 26 (10), pp. 1146-1153 (2008).
I. Braslavsky, B. Hebert, E. Kartalov, S. R. Quake, "Sequence Information Can Be Obtained from Single DNA Molecules," Proc. Natl. Acad. Sci. USA, vol. 100, pp. 3960-3964 (2003).
F. S. Collins, M. Morgan, A. Patrinos, "The Human Genome Project—Lessons From Large-scale Biology," Science, vol. 300, pp. 286-290 (2003).
M. Fedurco, A. Romieu, S. Williams, I. Lawrence, G. Turcatti, "BTA, a Novel Reagent for DNA Attachment on Glass and Efficient Generation of Solid-phase Amplified DNA Colonies," Nucleic Acids Res. vol. 34, pp. e22 (2006).
S. Harrer et al. "Electrochemical Characterization of Thin Film Electrodes Towards Developing a DNA-Transistor," Langmuir, vol. 26 (24), pp. 19191-19198 (2010).
T. D. Harris et al., "Single-molecule DNA Sequencing of a Viral Genome," Science, vol. 320, pp. 106-109 (2008).
J. J. Kasianowicz, E. Brandin, D. Branton, D. W. Deamer, "Characterization of Individual Polynucleotide Molecules Using a Membrane Channel," Proc. Natl. Acad. Sci. USA., vol. 93, pp. 13770-13773 (1996).
B. Luan, H. Peng, S. Polonsky, S. Rossnagel, G. Stolovitzky, and G. Martyna, "Base-by-base Ratcheting of Single-stranded DNA Through a Solid-state Nanopore," Phys. Rev. Lett., vol. 104 (23) pp. 238103-1-238103-4 (2010).
B. Luan, A. Aksimentiev, "Control and Reversal of the Electrophoretic Force on DNA in a Charged Nanopore," J. Phys. Condens. Matter, vol. 22, pp. 454123 (2010).
B. Luan, S. Harrer, A. Afzali, H. Peng, P. Waggoner, S. Polonsky, G. Stolovitzky, G. Martyna, "Tribological Effects on DNA Translocation in a SAM-Coated Nanochannel." J. Phys. Chem. B., vol. 114 (91), pp. 17172-17176 (2010).
M. Margulies et al., "Genome Sequencing in Mircrofabricated High-density Pico-litre Reactors," Nature, vol. 437, pp. 376-380 (2005).
F. Sanger, S. Nicklen, A. R. Coulson, "DNA sequencing with chain termination inhibitors," Proc. Natl. Acad. Sci USA., vol. 74 (12), pp. 5463-5467 (1977).
J. Shedure et al., "Accurate Multiplex Polony Sequencing of an Evolved Bacterial Genome," Science, vol. 309, pp. 1728-1732 (2005).
G. Turcatti, A. Romieu, M. Fedurco, A. P. Tairi, "A New Class of Cleavable Fluorescent Nucleotides: Synthesis and Optimization as Reversible Terminators for DNA Sequencing by Synthesis," Nucleic Acids Res., vol. 36, pp. e25 (2008).
B. Luan et al., "DNA-translocation through a solid state nanopore coated with a self-assembled monolayer," Bull. Am. Phys. Soc., APS March Meeting 2011, vol. 56, No. 1, Abstract V43.00002, Mar. 24, 2011, 1 page.
A. Bergvall et al., "Graphene nanogap for gate-tunable quantum-coherent single-molecule electronics," Phys. Rev. B, vol. 84, No. 15, 2011, 155451, 7 pages.
A. J. Storm et al., "Fabrication of solid-state nanopores with single-nanometre precision," Nature Materials, vol. 2, Aug. 2003, pp. 537-540.
Amit Meller et al., "Rapid nanopore discrimination between single polynucleotide molecules," PNAS, Feb. 1, 2000, vol. 97, No. 3, pp. 1079-1084.
Akeson, Mark, et al., "Microsecond Time-Scale Discrimination Among Polycytidylic Acid, Polyadenylic Acid, and Polyuridylic Acid as Homopolymers or as Segments Within Single RNA Molecules," Biophysical Journal, vol. 77, Dec. 1999, pp. 3227-3233.
Kasianowicz, John J., et al., "Characterization of individual polynucleotide molecules using a membrane channel", Proc. Natl. Acad. Sci. USA, vol. 93, Nov. 1996, pp. 13770-13773.
Lagerqvist, Johan et al., "Fast DNA Sequencing via Transverse Electronic Transport", Nano Lett., vol. 6, No. 4, revised Manuscript, pp. 779-782.
Soni, Gautam V. et al., "Progress toward Ultrafast DNA Sequencing Using Solid-State Nanopores", Clinical Chemistry, vol. 53, No. 11, (2007), pp. 1-6.
Douville, et al., "DNA Linearization Through Confinement in Nanofluidic Channels, Anal Bioanal Chem.", Aug. 2008; vol. 391; No. 7; pp. 2395-2409; Abstract; p. 2402, col. 2; para 5; p. 2406; col. 2; para 2; p. 2407; Fig. 5b.
Bae, S. et al., "Roll-to-Roll Production of 30-inch Graphene Films for Transparent Electrodes," Nature Nanotechnology, Published online: Jun. 20, 2010, 5 pages.
Branton D, Deamer D W, Marziali A, Bayley H, Benner S A, Butler T, Di Ventra M, Garaj S, Hibbs A, Huang X, Jovanovich S B, Krstic P S, Lindsay S, Ling X S, Mastrangelo C H, Meller A, Oliver JS, Pershin YV, Ramsey JM, Riehn R, Soni GV, Tabard-Cossa V, Wanunu M, Wiggin M, Schloss J A, "The Potential and Challenges of Nanopore Sequencing," Nature Biotechnology, Found online: http://www.nature.com/naturebiotechnology, 26(10) 1146-1153 (2008), 8 pages.
D. W. Hess, "Plasma-assisted oxidation, anodization, and nitridation of silicon," IBM J. Res. Develop. vol. 43. No. 1/2, Jan./Mar. 1999, pp. 127-145.
A. K. Geim and K. S. Novoselov, "The Rise of Graphene," Nature Materials 6, 183 (2007), 9 pages.
Gracheva M E, Xiong A, Aksimentiev A, Schulten K, Timp G and Leburton J P, "Simulation of the Electric Response of DNA Translocation Through a Semiconductor Nanopore-capacitor," Nanotechnology, Published Jan. 6, 2006, Online: stacks.iop.org/Nano/17/622; 12 pages.
S. Harrer et al., "Electrochemical Protection of Thin Film Electrodes in Solid State Nanopore," Nanotechnology, vol. 22, 2011, 275304, 6 pages.
J. Hass, W.A. De Heer and E.H. Conrad, "The Growth and Morphology of Epitaxial Multilayer Graphene," Journal of Physics: Condensed Matter 20, 323202 (2008), 28 pages.
Heng J B, Ho C, Kim T, Timp R, Aksimentiev A, Grinkova Y V, Sligar S, Schulten K and Timp G, "Sizing DNA Using a Nanometer-diameter Pore," Biophys Journal vol. 87, 2905-2911 (Oct. 2004); 7 pages.
H.W.C. Postma, "Rapid Sequencing of Individual DNA Molecules in Graphene Nanogaps," Nano Letters, vol. 10, No. 2, Jan. 4, 2010, pp. 420-425.
International Search Report—PCT; Notification of Transmittal of the International Search Report and the Written Opinion of the International Searching Authority, or the Declaration; dated Apr. 5, 2011; International application No. PCT/US1123872; pp. 1-8.
J. Prasongkit et al., "Transverse conductance of DNA necleotides in a graphene nanogap from first principles," arXiv:1012.1669v2 [physics.ins-det], [v1] Dec. 8, 2010, [v2] Jan. 14, 2011, Nano Lett., vol. 11, No. 5, 2011, pp. 1941-1945.
K.S. Kim, Y. Zhao, H. Jang, S. Y. Lee, J. M. Kim, K. S. Kim, J. H. Ahn, P. Kim, J. Y. Choi, B. H. Hong, "Large-Scale Pattern Growth of Graphene Films for Stretchable Transparent Electrodes," Nature 457, 706-710 (2009).
B. Luan et al., "Tribological Effects on DNA Translocation in a Nanochannel Coated with a Self-Assembled Monolayer," J. Phys. Chem. B, vol. 114, 2010, pp. 17172-17176.
M. J. Kim et al., "Rapid Fabrication of Uniformly Sized Nanopores and Nanopore Arrays for Parallel DNA Analysis," Adv. Mater. 2006, 18, pp. 3149-3153.
Novoselov K S et al, "Electric Field Effect in Atomically Thin Carbon Films" Science, American Association for the Advancement

(56) References Cited

OTHER PUBLICATIONS of Science, US, Washington, DC, vol. 306, No. 5696, Oct. 11, 2004, pp. 666-669, XP009086357, ISSN: 0036-8075, the whole document.

Fernando Patolsky, Gengfeng Zheng, Oliver Hayden, Melike Lakadamyali, Xiaowei Zhuang, and Charles M. Lieber, "Electrical detection of single viruses," Departments of Chemistry and Chemical Biology and Physics and Division of Engineering and Applied Sciences, Harvard University, Cambridge, MA 02138, Contributed by Charles M. Lieber, Aug. 20, 2004, pp. 1-6.

Polonsky et al., "Nanopore in metal-dielectric sandwich for DNA position control," Applied Physics Letters 91, 153103 (2007), pp. 1-3.

Schedin F et al: "Detection of Individual Gas Molecules Absorbed on Graphene" Nature Materials Nature Publishing Group, UK, vol. 6, No. 9, Sep. 2007, pp. 652-655, XP002506772, ISSN: 1476-1122, the whole document.

A. Sidorenko et al., "Controlled Switching of the Wetting Behavior of Bioimetic Surfaces with Hydrogel-Supported Nanostructures," J. Mater. Chem., vol. 18, 2008, pp. 3841-3846.

Eric Stern, James F. Klemic, David A. Routenberg, Pauline N. Wyrembak, Daniel B. Turner-Evans, Andrew D. Hamilton, David A. Lavan, Tarek M. Fahmy and Mark A. Reed, "Label-free immunodetection with CMOS-compatible semiconducting nanowires," Nature Publishing Group, vol. 445, Feb. 2007, doi:10.1038/nature05498, pp. 1-4.

A. J. Storm, J. H. Chen, X. S. Ling, H. W. Zandbergen and C. Dekker, "Fabrication of Solid-State Nanopores with Single-Nanometre Precision," Nature Materials 2, 537-540 (2003).

G. Tizazu et al., "Photopatterning, Etching, and Derivatization of Self-Assembled Monolayers of Phosphonic Acids on the Native Oxide of Titanium," Langmuir, vol. 25, 2009, pp. 10746-10753.

S. Vassanelli, P. Fromherz, "Transistor Probes Local Potassium Conductances in the Adhesion Region of Cultured Rat Hippocampal Neurons," The Journal of Neuroscience, Aug. 15, 1999, 19(16):6767-6773, Department of Membrane and Neurophysics, Max-Planck-Institute for Biochemistry.

G. Wang et al., "Photon Gated Transport at the Glass Nanopore Electrode," J. Am. Chem. Soc., vol. 128, 2006, pp. 13553-13558.

Written Opinion of the International Searching Authority; dated Apr. 5, 2011; pp. 1-6; International application No. PCT/US11/23872.

E. R. Mardis; "Next-Generation DNA Sequencing Methods"; Annu. Rev. Genom. Human Genet.; First published online as Review in Advance on Jun. 24, 2008; p. 387-402.

S. Chang; "Chemical Recognition and Binding Kinetics in a Functionalized Tunnel Junction"; Nanotechnology; vol. 23; p. 1-14; 2012.

\* cited by examiner

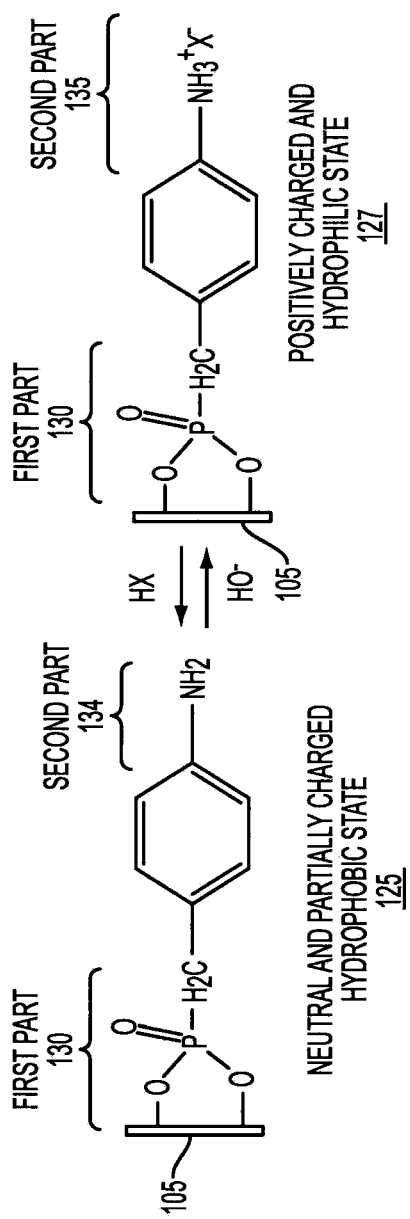

FIG. 6

TABLE 1

| Modulation reaction | Type I solution |
|---|---|
| neutral hydrophilic to negatively charged hydrophilic | 1 M KCl in water, ph 10 |
| negatively charged hydrophilic to neutral hydrophilic | dilute hydrochloric acid |
| neutral hydrophilic to neutral hydrophobic | trimethylsilyl diazomethane |

FUNCTIONALLY SWITCHABLE SELF-ASSEMBLED COATING COMPOUND FOR CONTROLLING TRANSLOCATION OF MOLECULE THROUGH NANOPORES

This invention was made with United States government support under contract number 5R01HG005110-02 awarded by the National Institute of Health. The government has certain rights in the invention.

BACKGROUND

The present invention relates generally to controlling molecules, and more specifically, to controlling molecules with a switchable self-assembled coating compound.

Nanopore sequencing is a method for determining the order in which nucleotides occur on a strand of deoxyribonucleic acid (DNA). A nanopore (also referred to a pore, nanochannel, hole, etc.) can be a small hole in the order of several nanometers in internal diameter. The theory behind nanopore sequencing is about what occurs when the nanopore is immersed in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be positioned around the nanopore so that DNA bases can be differentiated while the DNA passes through the nanopore.

The DNA can be driven through the nanopore by using various methods. For example, an electric field might attract the DNA towards the nanopore, and it might eventually pass through the nanopore. The scale of the nanopore can have the effect that the DNA may be forced through the hole as a long string, one base at a time, like thread through the eye of a needle. Recently, there has been growing interest in applying nanopores as sensors for rapid analysis of biomolecules such as deoxyribonucleic acid (DNA), ribonucleic acid (RNA), protein, etc. Special emphasis has been given to applications of nanopores for DNA sequencing, as this technology holds the promise to reduce the cost of sequencing below $1000/human genome. Two issues in nanopore DNA sequencing are controlling the translocation of DNA through the nanopore and differencing individual DNA bases.

SUMMARY

According to an embodiment, a nanodevice is provided. The nanodevice includes a fluidic cell, a membrane dividing the fluidic cell, and a nanopore formed through the membrane. The nanopore is coated with an organic compound. A first part of the organic compound binds to a surface of the nanopore, and a second part of the organic compound is exposed freely inside of the nanopore. The second part of the organic compound is configured to be switched among a first neutral hydrophilic end group, a second negatively charged hydrophilic end group, and a third neutral hydrophobic end group based on a switching mechanism.

According to an embodiment, a method for functionally switching an organic compound in a nanopore is provided. The method includes coating the nanopore in a nanodevice with the organic compound, and the nanodevice includes a fluidic cell, a membrane dividing the fluidic cell, and the nanopore formed through the membrane. A first part of the organic compound binds to a surface of the nanopore, and a second part of the organic compound is exposed freely inside of the nanopore. The method includes switching the second part of the organic compound among a first neutral hydrophilic end group, a second negatively charged hydrophilic end group, and a third neutral hydrophobic end group based on a switching mechanism.

According to an embodiment, a nanodevice is provided. The nanodevice includes a fluidic cell, a membrane dividing the fluidic cell, and a nanopore formed through the membrane. The nanopore is coated with an organic compound. A first part of the organic compound binds to a surface of the nanopore, and a second part of the organic compound is exposed freely inside of the nanopore. The second part of the organic compound is configured to be switched among a first neutral hydrophilic end group, a second negatively charged hydrophilic end group, and a third neutral hydrophobic end group. The first neutral hydrophilic end group is configured to be changed to the second negatively charged hydrophilic end group through a first switching mechanism. The second negatively charged hydrophilic end group is configured to be changed to the first neutral hydrophilic end group through a second switching mechanism. The first neutral hydrophilic end group is configured to be changed to the third neutral hydrophobic end group through a third switching mechanism.

Additional features and advantages are realized through the techniques of the present invention. Other embodiments and aspects of the invention are described in detail herein and are considered a part of the claimed invention. For a better understanding of the invention with advantages and features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIG. 1C illustrates the first and second parts of the organic coating compound in a neutral and partially charged hydrophobic state and in a positively charged and hydrophilic state according to an embodiment.

FIG. 6 is a table illustrating modulation reactions for respective solutions according to an embodiment.

DETAILED DESCRIPTION

Figure 1A:
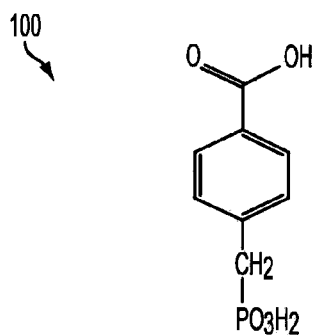
FIG. 1A illustrates a chemical structure for an organic coating compound of 4-carboxylbenzyl phosphonic acid according to an embodiment.

As one implementation, an embodiment provides ways to obtain motion control over DNA-molecules while they are translocating through solid state nanopores (which is a core requirement of all nanopore-based next generation DNA-sequencing technologies). The present disclosure has investigated and provides the impact of surface charge modulations inside coated nanopores on translocation behavior of DNA-molecules. Embodiments custom-design and synthesize the organic coating compound 4-carboxylbenzyl phosphonic acid (as one example) which is used to coat (e.g., a 5 nm-diameter) nanopore drilled into a (55-nm-thick $Si_3N_4$) membrane. Once the nanopore is coated with this compound (i.e., the organic coating compound 4-carboxylbenzyl phosphonic acid), the surface charge state of the nanopore can be switched back and forth between hydrophilic and hydrophobic functionality by flushing the nanopore with weak bases, and with dilute acids respectively. As one example, once a specific surface state was set, the coated pore was wetted with an aqueous 1 M (mole) KCl solution, and 20 nM (nanomoles) 2 kbp (kilo-basepairs which describe an entity of 1000 basepairs as a length unit for a DNA strand) dsDNA (double stranded DNA molecule) was used to perform translocation experiments. Translocation events were characterized and categorized for every surface charge state by monitoring the ionic current signal through the nanopore with focus on dwell time, event frequency, optimum translocation voltage (i.e. potential drop inside the nanopore at which the maximum event frequency is observed), open pore current vs. blockade current as well as the occurrence of DNA-sticking to the walls of the nanopore. Long-time sticking events of translocating DNA-molecules to the pore were observed in hydrophilic pores. According to an embodiment, changing the surface charge state of the coated nanopore from hydrophilic to hydrophobic fully eliminates DNA-sticking events and decreases the average dwell time by over 50%, thus enabling a smooth translocation behavior. Event frequency in hydrophobic pores decreases by 50% with respect to hydrophilic nanopores. Results of the present disclosure show that coating a solid state nanopore with 4-carboxylbenzyl phosphonic acid (and other acids as would be understood by one skilled in the art based on the present disclosure) and setting the surface charge state to hydrophobic enables fast and undisturbed DNA-translocation through such a nanopore disclosed herein.

It is noted that certain headings and subheading may be utilized for ease of understanding and for clarity to the reader. However, headings and subheading are not meant to be limiting in any way to the present disclosure.

I. Introduction

The information to produce many of the components of a cell such as RNAs and proteins is encoded in the sequence of nucleotides of the cell. Determining the DNA sequence is therefore fundamental to molecular biology and medicine. The most used technique for DNA sequencing has been the dideoxy termination method. Through parallelization, automation, and refinement of the established dideoxy sequencing method, the Human Genome Project is estimated to have cost $3 billion. Much lower cost methods for DNA sequencing will be required to make genome sequencing feasible for routine healthcare practice. Many new generation sequencing methods have been developed during the last decade, which represent significant advances over the traditional sequencing. Among them is a method based on threading a DNA molecule through a pore of a diameter of a few nanometers to sequence this molecule while it translocates through the nanopore which occupies a privileged place. DNA nanopore sequencing has the advantage of being a real-time single molecule DNA sequencing method with little to no sample preparation and inherently of low-cost. At least two technical roadblocks may prevent implementations of DNA nanopore nucleotide identification by electrical sensor methods: (i) the absence of a reliable approach to control the translocation of DNA through the nanopore, most importantly to eliminate sticking of DNA-molecules to the nanopore, and (ii) the technical difficulties in making sufficiently small sensors. The present disclosure describes an approach to controlling DNA translocation behavior inside a nanopore.

In one case, a device has been developed in which the device consists of a metal/dielectric/metal/dielectric/metal multilayer nano-structure built into the membrane that contains the nanopore. Voltage biases between the electrically addressable metal layers modulate the electric field inside the nanopore. This device utilizes the interaction of discrete charges along the backbone of a DNA molecule with the modulated electric field to trap DNA in the nanopore with single-base resolution. By cyclically turning on and off these gate voltages, it was previously shown by B. Luan, H. Peng, S. Polonsky, S. Rossnagel, G. Stolovitzky, and G. Martyna, in "Base-by-base ratcheting of single-stranded DNA through a solid-state nanopore," Phys. Rev. Lett., vol. 104 (23), pp. 238103-1-238103-4 (2010) which is herein incorporated by reference in its entirety. The plausibility to move DNA through the nanopore at a rate of one nucleotide per cycle was shown. This innovative device was called a DNA transistor, as a DNA current is produced in response to modulation of gate voltages in the device. The DNA transistor is then a DNA positional controlling platform with single-base-resolution, which can be used for sensor measurements. In that sense, the DNA transistor paves the way to nanopore-based nucleotide sequencing, and personalized medicine.

According to an embodiment, the present disclosure provides a custom-developed, synthesized, and experimentally tested organic nanopore coating compound that allows changing of the surface charge inside the nanopore by switching the functionality of the coating layer back and forth between hydrophilic and hydrophobic states in a controlled way. It is discussed how this coating scheme is a tool to eliminate sticking of DNA nucleotides to the surface of the nanopore. Additionally, as shown in our previous work, adding such an organic coating layer to a passivating oxide layer on TiN thin film electrodes inside nanopores suppresses the formation of residual nitrogen bubbles on the electrode surface (by S. Harrer, S. Ahmed, A. Afzali-Ardakani, B. Luan, P. S. Waggoner, X. Shao, H. Peng, D. L. Goldfarb, G. J. Martyna, S. M. Rossnagel, L. Deligianni, G. A. Stolovitzky, entitled "Electrochemical Characterization of Thin Film Electrodes Towards Developing a DNA Transistor," Langmuir, vol. 26 (24), pp. 19191-19198 (2010), and by S. Harrer, P. S. Waggoner, B. Luan, A. Afzali-Ardakani, D. L. Goldfarb, H. Peng, G. Martyna, S. M. Rossnagel, G. A Stolovitzky, entitled "Electrochemical protection of thin film electrodes in solid state nanopores," Nanotechnology, vol. 22. pp. 275304-1-6 (2011), both of which are herein incorporated by reference in their entirety). The coating technology of embodiments can serve (but is not limited to) three purposes: (i) it counteracts unwanted interaction between translocating DNA molecules and the nanopore surface such as for example long-time sticking effects, (ii) it provides the foundation for the studying of wanted interaction between translocating DNA molecules and the nanopore surface towards exploring the best electrical sensor that can resolve the difference between the four DNA nucleotides, and (iii) it contributes to electrochemical passivation of thin film electrodes inside a nanopore.

II. Nanopore Coating Scheme for Surface Charge Control

In preparation for designing and synthesizing a suitable nanopore coating compound, the impact of surface charge modulation was investigated inside a nanopore on DNA-translocation behavior (e.g., theoretically by means of all atom molecular dynamics simulations). Theoretical simulation results and their implementation into the organic coating compound that were used for DNA-translocation experiments are described in the following two sections for ease of understanding and not limitation.

A. Example Simulations

The surface charge of a nanopore affects not only the radial motion of DNA via electric interaction but also the motion of DNA along the channel (i.e., pore) axis due to an electroosmotic flow between charged DNA and pore surfaces. Molecular dynamics simulation (e.g., by B. Luan, A. Aksimentiev, in "Control and reversal of the electrophoretic force on DNA in a charged nanopore," J. Phys. Condens. Matter, vol. 22, pp. 454123 (2010) which is herein incorporated by reference in its entirety) shows that, when the surface charge density changes from positive to negative values, the effective driving force on DNA decreases (i.e., the translocation velocity decreases). This results from the motion of counterions on both charged DNA and nanopore surfaces in an electric field. For example, a negatively charged DNA molecule can be attracted by a positively charged nanopore surface, dramatically slowing down or even immobilizing DNA in the nanopore. Even for a neutral nanopore, the radial motion of DNA can also be affected by the hydrophobic interaction. Molecular dynamics simulation (e.g., by B. Luan, S. Harrer, A. Afzali, H. Peng, P. Waggoner, S. Polonsky, G. Stolovitzky, G. Martyna, in "Tribological Effects on DNA Translocation in a SAM-Coated Nanochannel" J. Phys. Chem. B., vol. 114 (91), pp. 17172-17176 (2010) which is herein incorporated by reference in its entirety) shows that ssDNA (single-stranded DNA molecules) can be stuck on a nanopore surface coated with a hydrophilic octanol-self-assembled-monolayer. However, if the nanopore surface is coated with a hydrophobic octane-self-assembled-monolayer, ssDNA can move freely in the radial direction. This also can apply to a dsDNA molecule (double stranded DNA molecule).

B. Synthesis of Coating Material

Based on the simulation results described above, the present disclosure has developed and synthesized the organic coating compound 4-carboxylbenzyl phosphonic acid whose chemical structure is shown as organic coating compound 100 in FIG. 1A. As one example, coating of a nanopore (e.g., nanopore 205 in FIG. 2) drilled into a $Si_3N_4$ membrane is achieved by immersing the membrane (e.g., membrane 105 in FIG. 2) into an aqueous solution containing the organic coating compound 100 for 24 hours and rinsing the nanopore with Isopropanol afterwards (to result in the membrane 105 shown in FIG. 2).

Figure 1B:
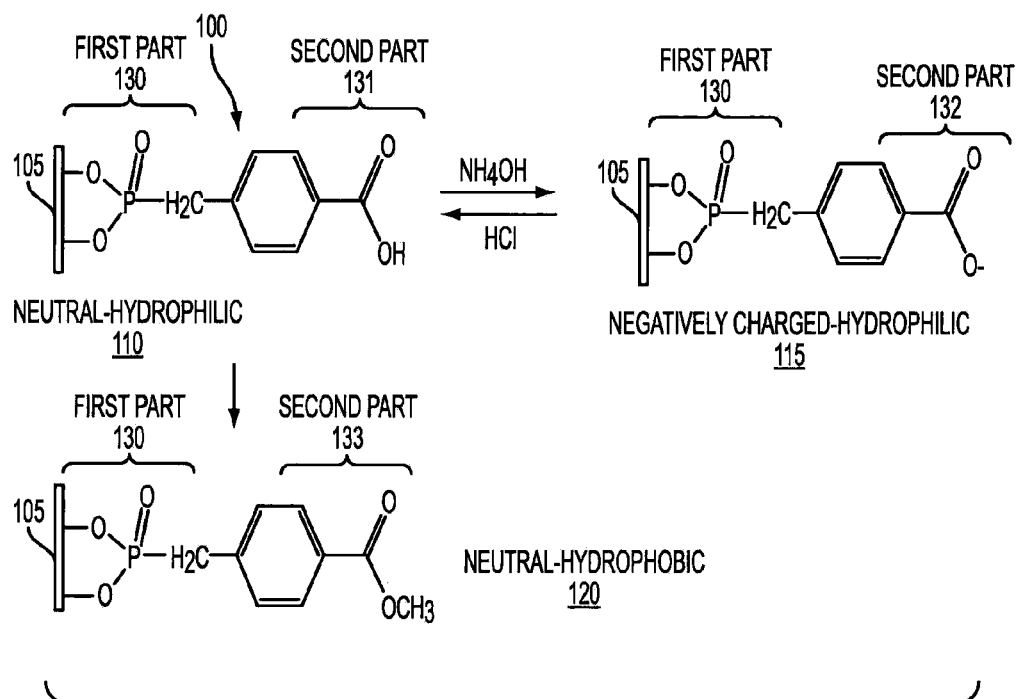
FIG. 1B illustrates the first and second parts of the organic coating compound in a neutral hydrophilic state, a negatively charged hydrophilic state, and a neutral hydrophobic state according to an embodiment.

FIG. 1B shows the organic coating compound 100 attached to the membrane 105 (which forms the nanopore 205) with a neutral hydrophilic state 110. In the neutral hydrophilic state 110, the phosphonic acid group (first part 130) covalently and exclusively bonds to the $Si_3N_4$ membrane surface 105 and exposes the carboxylic acid group which is hydrophilic and neutral (second part 131). The second part 131 of the neutral hydrophilic state 110 is a neutral hydrophilic end group.

Treatment of the organic coating compound 100 (in the neutral hydrophilic state 110) with weak bases like ammonia converts the carboxylic acid to a negatively charged carboxylate for a negatively charged hydrophilic state 115 in FIG. 1B. Now, the second part 131 of the organic coating compound 100 has been changed to a negatively charged hydrophilic end group in the second part 132.

Further treatment with dilute acid converts the (organic coating compound 100) negatively charged carboxylate (second part 132) back to the carboxylic acid (second part 131) to be in the neutral hydrophilic state 110. The second part 132 has been changed back to the neutral hydrophilic end group for the second part 131.

Additional treatment on the (carboxylic acid of) organic coating compound 100 in the neutral hydrophilic state 110 causes the carboxylic acid to be esterified (second part 133) to form methyl ester which is neutral and hydrophobic for the neutral hydrophobic state 120. The second part 133 has a neutral hydrophobic end group.

FIG. 1C shows the organic coating compound 100 attached to the membrane 105 (which forms the nanopore 205) with a neutral and partially charged hydrophobic state 125 (i.e., moderately hydrophobic state). Treatment of the organic coating compound 100 with HX (which represents HCl, HBr, HI, and/or any strong inorganic acid as understood by one skilled in the art) causes the neutral and partially charged hydrophobic end group of the second part 134 to be changed to the positively charged and hydrophilic end group of the second part 135 (for the positively charged and hydrophilic state 127).

The —$NH_2$ group (of the second part 134) is partially charged between pH 7-9 and moderately hydrophobic (i.e., in the neutral and partially charged hydrophobic state 125), and when the —$NH_2$ is converted to its salt by treatment with acids (HX), the —$NH_2$ (of the organic coating 100) becomes positively charged and hydrophilic. The organic coating 100 in the positively charged and hydrophilic state 127 is converted back to the neutral and partially charged hydrophobic state 125 (i.e., moderately hydrophobic state) by treatment with $HO^-$.

According to embodiments, all of these transformations can be achieved inside the nanopore 205 by flushing the coated nanopore 205 with weak bases, or dilute acids respectively, followed by a wait time of 24 hour. The switching time (between states 110, 115, and 120 as discussed herein) can be decreased to 20 minutes by applying a voltage of 100 mV (of voltage source 225 in FIG. 2) between cis- and trans-reservoirs (e.g., top and bottom) after flushing. It is to be pointed out that one can switch the same coated nanopore 205 back and forth between the neutral hydrophilic state 110 and the negatively charged hydrophilic state 115 multiple times, and switch the nanopore 205 between the neutral hydrophilic state 110 and the neutral hydrophobic state 120.

In chemistry, hydrophobicity is the physical property of a molecule (known as a hydrophobe) that is repelled from a mass of water. Hydrophobic molecules tend to be non-polar and, thus, prefer other neutral molecules and non-polar solvents. Hydrophobic molecules in water often cluster together, forming micelles. However, a hydrophile is a molecule or other molecular entity that is attracted to, and tends to be dissolved by, water. A hydrophilic molecule or portion of a molecule is one that has a tendency to interact with or be dissolved by water and other polar substances. A hydrophilic molecule or portion of a molecule is one that is typically charge-polarized and capable of hydrogen bonding, enabling it to dissolve more readily in water than in oil or other hydrophobic solvents. Hydrophilic and hydrophobic molecules are also known as polar molecules and nonpolar molecules, respectively.

III. Measuring Platform

Figure 2:
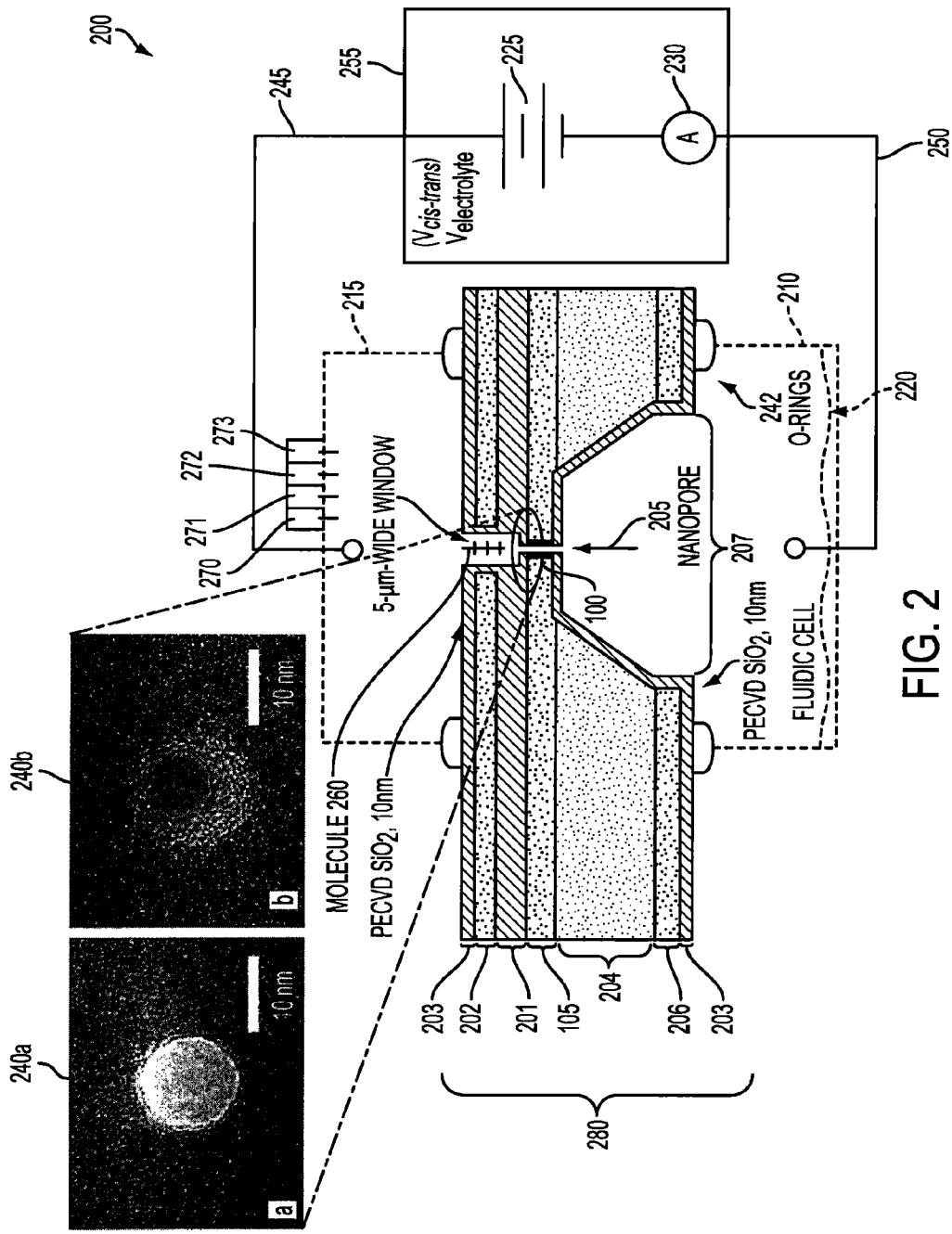
FIG. 2 is a cross-sectional view of a nanodevice having a nanopore coated with the organic coating compound according to an embodiment.

In order to study DNA translocation behavior through coated nanopores, the present disclosure presents the custom designed and fabricated measuring platform schematically shown in FIG. 2 as a cross-sectional view of nanodevice 200 according to one implementation.

The components of the device 200 are the 50-nm-thick silicon nitride (SiN) membrane 105 with the nanopore 205 drilled through the membrane 105, a fluidic cell 210 for mounting the membrane 105 and connecting the ends of the nanopore 205 to two reservoirs 215 and 220 which are in turn connected to an electronic pore current measuring setup of a voltage source 225 and ammeter 230. Layers 280 separate the two reservoirs 215 and 220. Note that the organic coating compound 100 component (only) adheres to SiN surfaces (of the membrane 105), and thus the (only) portion of the device 200 (platform) that is coated is the inner (membrane 105) surface of the nanopore 205. The membrane 105 is not conductive and thus does not constitute a thin film electrode (in this implementation). The only electric potential present in the aqueous electrolyte/DNA solution 235 is applied between the two reservoirs 215 and 220 of the fluidic cell 210 by the voltage source 225. The inserts 240a and 240b respectively show the same nanopore 205 after drilling and before coating with the organic coating compound 100 (at 240a), and after drilling and after coating with the organic coating compound 100 (at 240b).

Two Ag/AgCl electrodes 245 and 250 are immersed into the reservoirs 215 and 220 (of the fluidic cell 210) and electronically connect the fluidic cell 210 (also referred to as a flow cell) to an ionic current measurement setup (e.g., computer setup 255) including, e.g., a computer controlled patch clamp amplifier (Axon Axopatch™ 200B, by Molecular Devices), and a DAQ card (Digidata® 1440A, by Molecular Devices). The computer setup 255 is configured to apply a voltage (e.g., $V_{cis\ to\ trans}$) by the voltage source 225 to the electrodes 245 and 250 generating an electric field between the two reservoirs 215 and 220 through the wetted nanopore 205, threading electrolyte ions (of the solution 235) and DNA molecules 260 through the nanopore 205; thus creating an ionic current flow through the nanopore 205. Every time the DNA molecule 260 translocates through the nanopore 205, the monitored ionic current signal (measured by ammeter 230) shows a distinct peak varying in duration and shape depending on the type of translocation event (e.g., fast (non-sticking) events, long-time sticking events, and/or some combination thereof) of the DNA molecule 260. Note that the organic coating compound 100 component only adheres to $Si_3N_4$ surfaces (and SiN surfaces), and thus the only portion of the platform (i.e., device 200) that is coated is the inner surface of the nanopore 205.

All observed translocation effects are therefore exclusively due to interactions of DNA molecules (such as DNA molecule 260) with the coated surface areas inside the nanopore 205.

The device 200 also has o-rings 242 sealing fluidic cell 210 to the layers 280 (e.g., sealing the top reservoir 215 and bottom reservoir 220 to the layers 280).

A. Nanopore Fabrication

The fabrication of the nanopore membrane 105 shown in FIG. 2 may start from a conventional 750-μm-thick 200-mm-diameter (100) Si wafer as layer 204. First, low pressure chemical vapor deposition (LPCVD) is used to deposit low stress 50-nm-thick SiN on both sides (membrane/layer 105 on top (what you see on the bottom depicted as layer 206 is what is actually the cumulated layers of SiN & $Si_3N_4$ layers which are deposited onto the backside throughout the fabrication process.) of the Si wafer, and then 350 nm $Si_3N_4$ is deposited on the backside of the Si wafer using plasma enhanced chemical vapor deposition (PECVD) technology. 200-nm-thick PECVD $SiO_2$ (layer 201) and 200-nm-thick PECVD $Si_3N_4$ (layer 202) are deposited sequentially on the front side of the Si wafer. Then a square hole is etched through the 400-nm-thick $Si_3N_4$ (350 nm PECVD $Si_3N_4$ plus 50 nm LPCVD SiN) on the backside of the wafer into the Si substrate by reactive ion etching (RIE). The Si wafer is then put into 80° C. 25% (w/w) TMAH solution to etch the backside Si. This is an anisotropic etch with the etch rate in (100) direction being much larger than the one in (111) direction. Hence, an inverted pyramid 207 is etched into Si before the etch stops on the 50-nm-thick LPCVD $Si_3N_4$, forming a 100 μm×100 μm square-shaped free standing membrane made of 50 nm $Si_3N_4$, 200 nm $SiO_2$, and 200 $Si_3N_4$ (from bottom to top) (i.e., layers 105, 201, and 202).

A 5-μm-diameter hole (window) is made at the center of the free-standing membrane, which etches through the top two layers 201 and 202 (200 $Si_3N_4$ and 200 nm $SiO_2$) and creates a free-standing membrane 105 area made of 50-nm-thick SiN and comprising a diameter of 5 μm. 10-nm-thick PECVD $SiO_2$ (layer 203) is then deposited on both sides of the wafer (including the membrane area), so that the 5-μm-diameter free-standing membrane is made of 10 nm $SiO_2$, 50 nm SiN, and 10 nm $SiO_2$ (which is top layer 203, membrane 205, and bottom layer 203). A nanopore 205 (typical diameters range from 3 nm to 10 nm) is then drilled through the free-standing membrane 105 using a focused electron beam in a transmission electron microscope (JEOL 3000F).

B. Electrochemical Solutions

Two types of solutions 235 were employed in various experiments: (i) type I solutions were used for flushing (i.e., treatment) coated nanopores 205 to change surface charge states (among surface charge states 110, 115, and 120) between translocation experiments, and (ii) a type II solution was inserted into nanopore 205 and fluidic cell (flow cell) during translocation experiments.

While type I solutions did not contain DNA molecules, type II solution comprised 1M KCl and 20 nM 2 kbp dsDNA molecules (e.g., molecule 260), and it is understood by one skilled in the art that other types of molecules may be utilized in a suitable solution. Water was used as solvent in both solutions (i.e., type I and II). FIG. 6 is a block diagram 600 of Table 1 which shows the type I solutions that were utilized to trigger respective switching reactions for states 110, 115, and 120. In FIG. 6, Table 1 shows the surface charge modulation reactions for nanopores (e.g., nanopore 205) coated with 4-carboxylbenzyl phosphonic acid (i.e., organic coating compound 100) and their respective flushing agents.

The type II solution (filled with 1M KCl and 20 nM 2 kbp dsDNA) is in pump 270 and can be pumped into and extracted from the fluidic cell 210 as desired. The type I solutions are respectively in pump 271 (filled with 1 M KCl in water, ph 10), pump 272 (filled with dilute hydrochloric acid), and pump 273 (filled with trimethylsilyl diazomethane). The type I solutions in pumps 271, 272, and 273 (along with type II solution in pump 270) can be respectively pumped into and out of the fluidic cell 210 as desired to cause a reaction of the organic coating compound 100 attached to the inside (to membrane 105) of the nanopore 205 as discussed for states 110, 115, and 120. Note that although pumps 270, 271, 272, and 273 are illustrated, these pumps may include any type of device configured to inject and/or withdraw the desired solution/flushing agent. For example, the pumps 270, 271, 272, and 273 may be a syringe with a plunger that fits tightly in a tube. The plunger can be pulled and pushed along inside a cylindrical tube (called a barrel), allowing the syringe to take in and expel a liquid or gas through an orifice at the open end of the tube. The open end of the syringe may be fitted with a hypodermic needle, a nozzle, or tubing to help direct the flow into and out of the barrel, which is then expelled to and/or extracted from the fluidic cell 210.

IV. DNA-Translocation Measurements

Translocation events through coated nanopores (such as nanopore 205) using type II solution (having DNA molecule 260 via, e.g., pump 270) were characterized and categorized for every surface charge state by monitoring the ionic current signal through the nanopore continuously for 10 min. Thereby, ionic current drops are caused by DNA molecules 260 translocating through the nanopore 205 and thus partially blocking the nanopore 205, when a voltage is applied by the voltage source 225. This detection technique for translocation events through nanopores is well established and has been proven to be a powerful tool for studying translocation behavior of DNA-molecules through nanopores; further information can be found in J. J. Kasianowicz, E. Brandin, D. Branton, D. W. Deamer, "Characterization of individual polynucleotide molecules using a membrane channel," Proc. Natl. Acad. Sci. USA., vol. 93, pp. 13770-13773 (1996), which is herein incorporated by reference in its entirety.

One example case defines the optimum applied translocation voltage $V_{cis\ to\ trans}$ (at which the event frequency reaches its maximum), dwell time, event frequency, open pore current (ionic current through the pore without DNA blockage), blockade current, as well as the occurrence of DNA-sticking to the walls of the nanopore 205 as characteristic features of each observed translocation event. Ionic current data was collected at an initial scan rate of 250 kHz which then was modulated by a 2 kHz low pass filter.

All current traces shown in this section below are representative snapshots from continuous 10 min long traces and chosen to reflect the translocation behavior during the complete 10 min long experiment in a shorter, condensed manner. While this section qualitatively describes experimental translocation event data for each of the three different surface charge states using the same coated nanopore (e.g., the nanopore 205 as shown in FIG. 2) a detailed quantitative statistical data analysis will be given in the following section below. It is noted that although some experimental data is discussed for explanation purposes and ease of understanding, the present disclosure is not meant to be limited.

The three (reversible) states of the organic coating compound 100 in the nanopore 205 will be discussed which are the neutral hydrophilic state 110, the negatively charged hydrophilic state 115, and the neutral hydrophobic state 120, where the nanopore 205 has been flushed with the respective (flushing agent) type I solution as discussed in Table 1 and FIG. 1B. Subsequently, the type II solution is injected to test the desired molecules 260.

A. Neutral Hydrophilic Pore

The neutral hydrophilic pore is when the nanopore 205 is coated with the organic coating compound 100 and is in the neutral hydrophilic state 110. In one case, this may be the initial state of the organic coating compound 100 attached to the inside surface of the nanopore 205 and/or in another case, this is when the nanopore 205 has been flushed with dilute hydrochloric acid to change to the neutral hydrophilic state 110 (from the negatively charged hydrophilic state 115).

Figure 3:
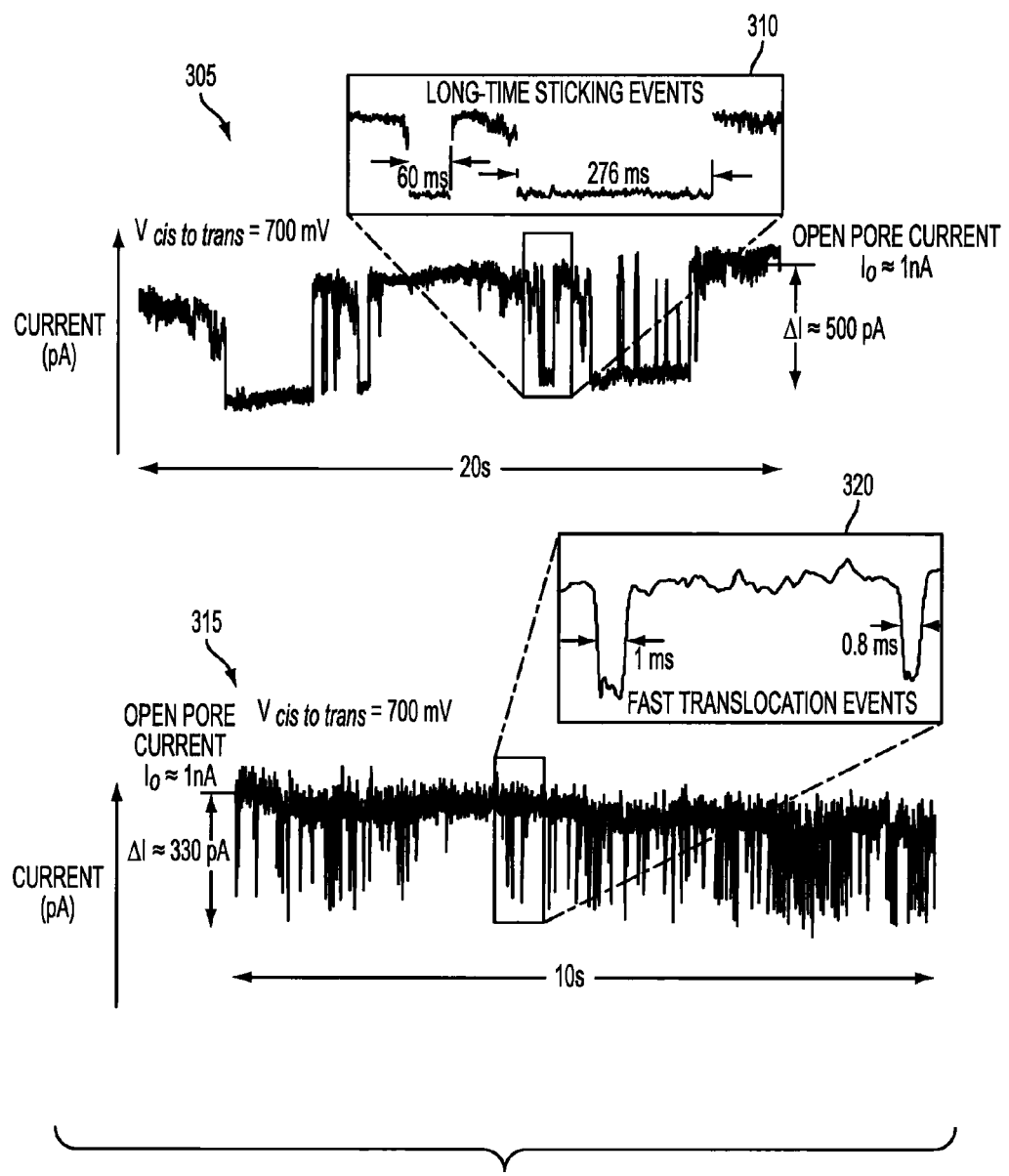
FIG. 3 is a waveform diagram illustrating neutral hydrophilic translocation event traces according to an embodiment.

FIG. 3 shows experimental results of DNA-translocation experiments by means of two recordings (illustrated in waveforms 305 and 315) of the ionic pore current signal trace (e.g., via the ammeter 230) using the neutral hydrophilic nanopore (e.g., the nanopore 205 with the organic coating 100 in the neutral hydrophilic state 110). The optimum translocation voltage $V_{cis\ to\ trans}$ was 700 mV (applied by voltage source 225), and the open pore current $I_0$ (e.g., with no DNA molecule 260 in the nanopore 205) was approximately 1 nA. There was observed two types of translocation events (of the DNA molecule 260): long-time sticking events and fast non-sticking events. The majority of observed events are sticking events indicating strong interaction between the translocating DNA-molecules 260 and the coated surface of the nanopore 205. This (unwanted) interaction compromises smooth translocation behavior. Even when operating the nanopore 205 at the optimum translocation voltage, long-time DNA sticking to the coating layer may not be eliminated (in one case). Event frequency was measured to be 80 Hz for non-sticking events. Blockade currents ranged between 330 pA for non-sticking events and 500 pA for sticking events.

In waveform 305 in FIG. 3, a neutral hydrophilic translocation event trace shows long-time sticking events in which the ionic pore current signal was monitored for 20 seconds. The long-time current drops with durations ranging from approximately 60 Ms-280 ms (as shown in enlarged window 310) are caused by DNA molecules sticking to the coated wall of the nanopore 205 while translocating through and thus partially blocking it.

In waveform 315, a neutral hydrophilic translocation event trace shows fast non-sticking events in which the ionic pore current signal was monitored for 10 s. Short current drops with durations ranging from approximately 0.8 ms-1 ms (as shown in enlarged window 320) are caused by DNA molecules 260 smoothly translocating through the nanopore 205 without sticking of DNA to the walls of the nanopore 205.

The inserts in windows 310 and 320 show close-up views of the parts of the translocation traces which are delineated by rectangles. Blockade currents for fast events (with a change in current of approximately 330 pA) were slightly smaller than blockade currents (with a change in current of approximately 500 pA) caused by DNA sticking (e.g., sticking events) to the walls of the nanopore 205.

B. Negatively Charged Hydrophilic Pore

The negatively charged hydrophilic pore is when the nanopore 205 is coated with the organic coating compound 100 and is in the negatively charged hydrophilic state 115. This may be when the nanopore 205 has been flushed (with 1 mole of KCl in water (ph 10) and/or $NH_4OH$) to change from the neutral hydrophilic state 110 to the negatively charged hydrophilic state 115.

Figure 4:
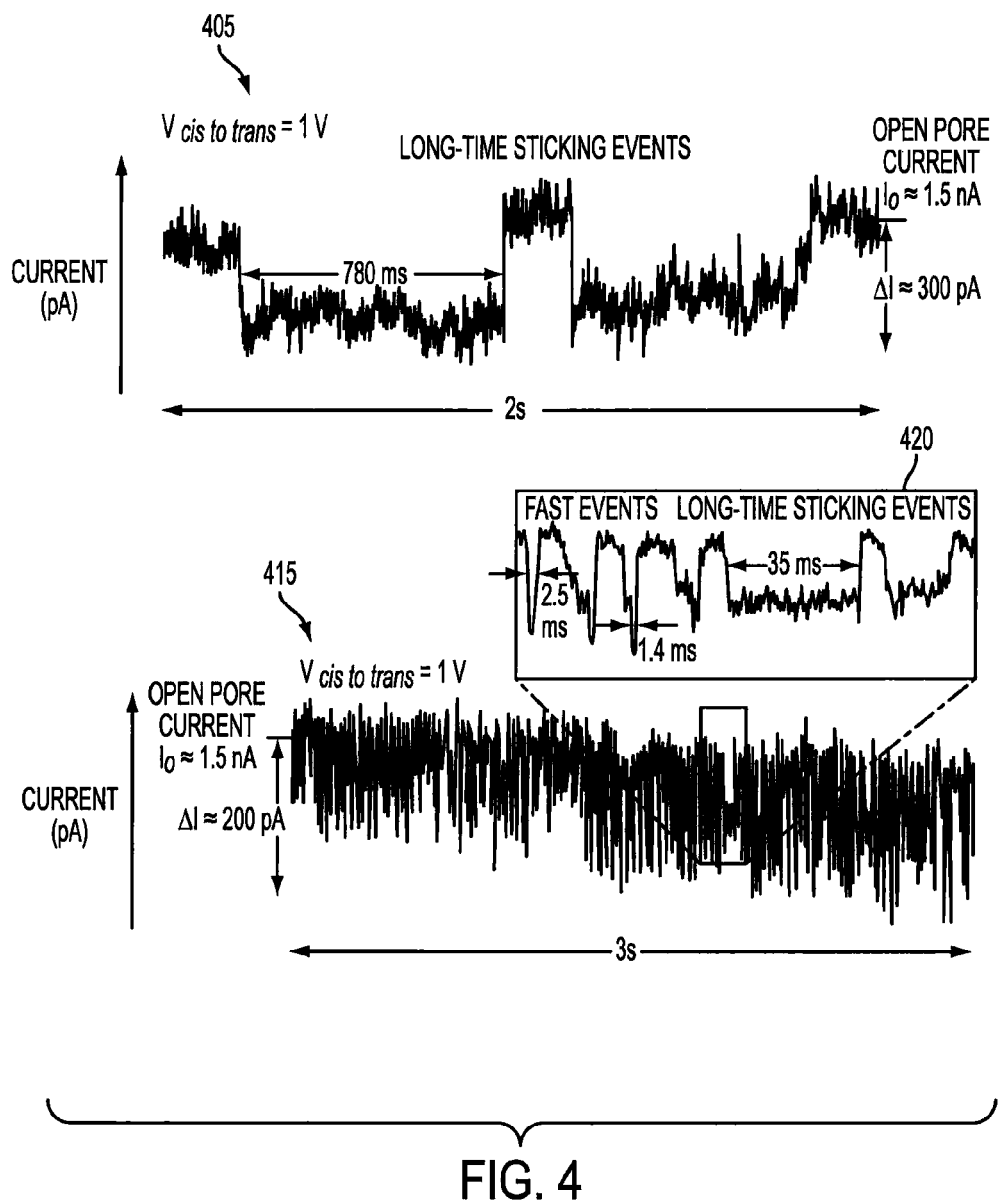
FIG. 4 is a waveform diagram illustrating negatively charged hydrophilic translocation event traces according to an embodiment.

FIG. 4 shows the experimental results of DNA-translocation experiments by means of two recordings (illustrated in waveforms 405 and 415) of the ionic pore current signal trace using the negatively charged hydrophilic nanopore 205. The open pore current $I_O$ was 1.5 nA at the optimum translocation voltage $V_{cis\ to\ trans}$ of 1 V (e.g., applied by the voltage source 225). Both, $I_O$ as well as $V_{cis\ to\ trans}$ (in FIG. 4) were significantly larger than for the neutral hydrophilic pore in FIG. 3. This can be explained by the additional entrance barrier generated by the negative surface charge of the nanopore 205 that needs to be overcome by a larger translocation voltage (of the voltage source 225) for threading DNA-molecules into the nanopore 205. Similar to results obtained from the neutral hydrophilic state 110, two types of translocation events were observed: long-time sticking events and fast non-sticking events. However, as opposed to the neutral hydrophilic state 110, the majority of observed events are non-sticking events in the negatively charged hydrophilic environment (i.e., negatively charged hydrophilic state 115), and this shows improved translocation behavior. Note that even when operating the nanopore 205 at the higher translocation voltage in order to create a cis-trans potential gradient high enough to overcome the added negative entrance potential, long-time sticking events still (may) occur and can be explained as follows. The electric dragging force is strong enough to initially thread DNA-molecules into the nanopore 205 but is then (possibly) too weak to prevent occasional sticking while the translocating DNA-molecule passes by the coating layer. Event frequency was measured to be 158 Hz for non-sticking events. This significantly higher event frequency can be explained by the higher translocation voltage. Blockade currents ranged between 200 pA for non-sticking events in waveform 405 and 300 pA for sticking events in waveform 415, and thus were slightly smaller than for neutral hydrophilic blocking events.

In waveform 405, the negatively charged hydrophilic translocation event trace shows long-time sticking events in which the ionic pore current signal was monitored for 2 seconds. The long-time current drops with durations of close to 1 s are caused by DNA molecules sticking to the coated wall of the nanopore while translocating through and thus partially blocking it.

In waveform 415, the negatively charged hydrophilic translocation event trace shows fast non-sticking events and one long-time sticking event (as shown in enlarged window 420). In waveform 415, the ionic pore current signal was monitored for 3 s, and short current drops with durations ranging from 1.4 ms-2.5 ms are caused by DNA molecules smoothly translocating through the nanopore 205 without sticking of DNA to the walls of the nanopore 205. Similar to results obtained from the neutral hydrophilic state 110, blockade currents for fast events (in waveform 415) were slightly smaller than blockade currents caused by DNA sticking (in waveform 405) to the walls of the nanopore. Generally, blockade currents were smaller in negatively charged hydrophilic pores than in neutral hydrophilic pores.

C. Neutral Hydrophobic Pore

The neutral hydrophobic pore is when the nanopore 205 is coated with the organic coating compound 100 and is in the neutral hydrophobic state 120. This may be when the nanopore 205 has been flushed (with trimethylsilyl diazomethane) to change from the neutral hydrophilic state 110 to the neutral hydrophobic state 120.

Figure 5:
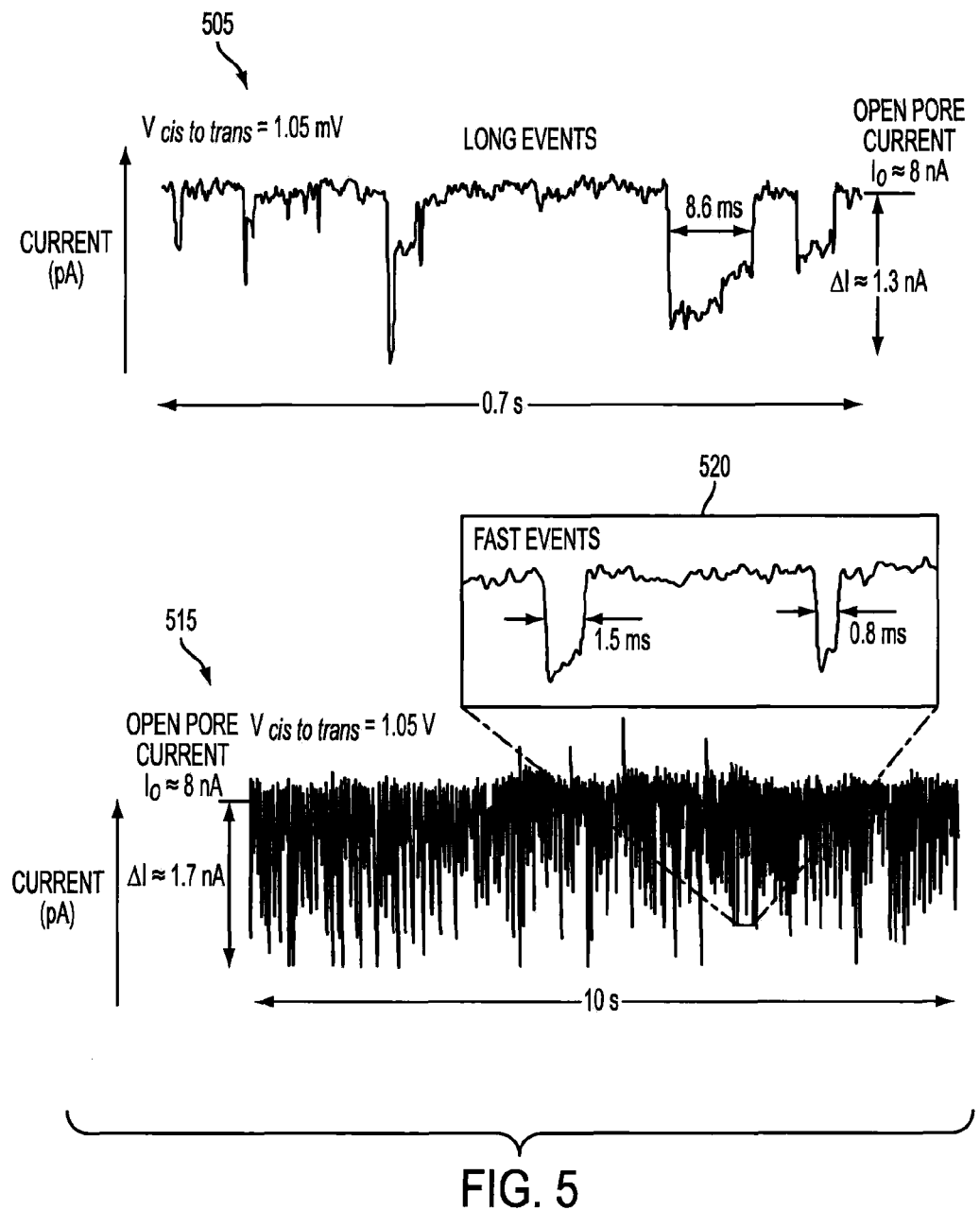
FIG. 5 is a waveform diagram illustrating neutral hydrophobic translocation event traces according to an embodiment.

FIG. 5 shows the experimental results of DNA-translocation experiments by means of two recordings (shown in waveforms 505 and 515) of the ionic pore current signal trace using the neutral hydrophobic nanopore. The optimum translocation voltage $V_{cis\ to\ trans}$ was 1.05 V (applied by the voltage source 225) and is larger than for the negatively charged hydrophilic pore in FIG. 4. This can be explained by the further increased entrance barrier generated by the hydrophobic surface charge of the nanopore 205 that needs to be overcome by an even larger translocation voltage for threading DNA molecules 260 into the nanopore 205. The open pore current $I_O$ increased to 8 nA, i.e., was significantly larger than for both hydrophilic pore states (e.g., neutral hydrophilic state 110 and negatively charged hydrophilic state 115). As opposed to both hydrophilic states (neutral hydrophilic state 110 and negatively charged hydrophilic state 115), there were not any observed long-time sticking events but only fast non-sticking events. Long-time sticking of DNA-molecules to the coated nanopore 205 surface was completely eliminated at the optimum translocation voltage. The absence of sticking effects demonstrates that the coating compound 100 should be operated in its (neutral) hydrophobic state to ensure unperturbed translocation behavior of DNA-nucleotides through the coated solid state nanopore 205, but is not limited to hydrophobic state.

Event frequency was measured to be 37 Hz. This significantly decreased event frequency can be explained by the extremely high entrance barrier that is created by the hydrophilic nanopore 205 surface. Blockade currents ranged between 1.3 nA (as shown in waveform 505) and 1.7 nA (in waveform 515), and thus were significantly larger than for all hydrophilic blocking events (in FIGS. 3 and 4).

In waveform 505, the neutral hydrophobic translocation event trace shows close-ups of only fast non-sticking events in which the ionic pore current signal was monitored for 0.7 s, and current drops having durations between 0.8 ms-8.6 ms were observed.

In an enlarged window 520 of the waveform 515, the neutral hydrophobic translocation event trace again shows exclusively non-sticking events in which the ionic pore current signal was monitored for 10 s, where short current drops with durations ranging from approximately 0.8 ms-1.5 ms are caused by DNA molecules smoothly translocating through the nanopore 205 without sticking of DNA to the walls of the nanopore 205.

Generally, blockade currents were larger in hydrophobic pores (e.g., the neutral hydrophobic state 120) than in hydrophilic pores (e.g., the neutral hydrophilic state 110 and the negatively charged hydrophilic state 115). The complete absence of long-time sticking events (in FIG. 5) at the optimum translocation voltage proves that hydrophobic pores are the optimum platform for enabling unperturbed DNA-translocation (in this example).

Although example experimental data is discussed at times, it is understood that the present disclosure is not limited to the example experimental data. Examples are simply provided for ease of understanding and not limitation.

Figure 7:
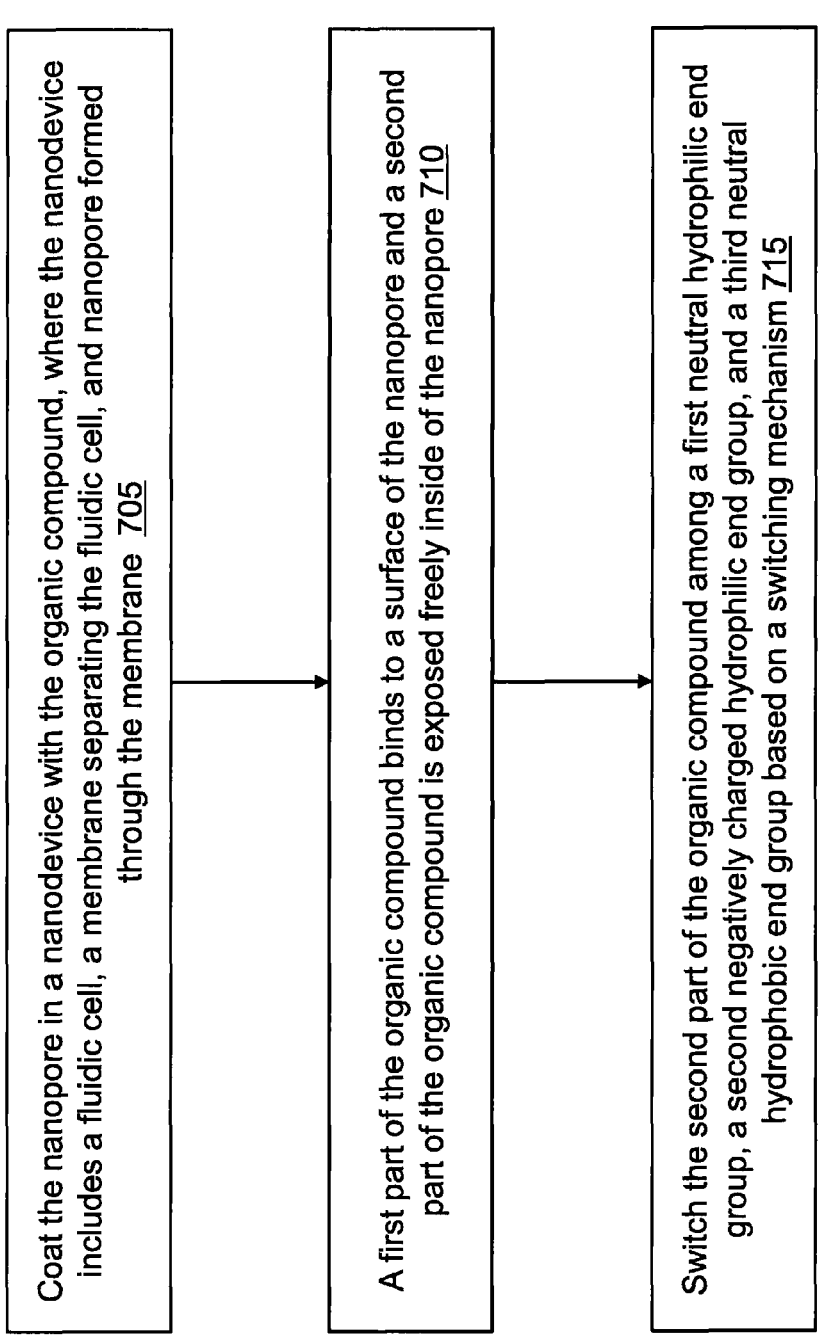
FIG. 7 is a flow chart illustrating a method for functionally switching the state of an organic coating compound in a nanopore to control the translocation of a molecule through/in the nanopore according to an embodiment.

FIG. 7 is a flow chart of a method 700 for functionally switching an organic compound (such as the organic coating compound 100) in the nanopore 205 according to an embodiment. Reference can be made to FIGS. 1-6.

The nanopore 205 (in the nanodevice 200) is coated with the organic compound 100 at block 705. The nanodevice 200 includes the fluidic cell 210, a membrane 105 (which is part of the layers 280) separating the fluidic cell 210 (into top and bottom reservoirs 215 and 220), and the nanopore formed through the membrane 105.

A first part (e.g., the first part 130) of the organic compound 100 binds to a surface of the nanopore 205 and a second part (e.g., the second part 131) of the organic compound is exposed freely inside of the nanopore 205 at block 710.

At block 715, the second part 131 of the organic compound 100 is switched among a first neutral hydrophilic end group (e.g., the second part 131), a second negatively charged hydrophilic end group (e.g., the second part 132), and a third neutral hydrophobic end group (e.g., the second part 133) based on a switching mechanism (e.g., the flushing agent/solution in pumps 271, 272, and 273).

Based on the switching mechanism, the second part of the organic compound is also configured to be switched among a fourth neutral and partially charged hydrophobic end group in addition to the first neutral hydrophilic end group, the second negatively charged hydrophilic end group, and the third neutral hydrophobic end group.

The first neutral hydrophilic end group (e.g., second part 131) is configured to be changed to the second negatively charged hydrophilic end group (e.g., second part 132) through a first switching mechanism of the switching mechanism, and the first switching mechanism includes flushing the nanopore 205 with a solution containing 1 M KCl in water at ph 10 via the pump 271.

The second negatively charged hydrophilic end group (e.g., second part 132) is configured to be changed to the first neutral hydrophilic end group (e.g., second part 131) through a second switching mechanism of the switching mechanism, and the second switching mechanism includes flushing the nanopore 205 with a solution containing dilute hydrochloric acid via the pump 272.

The first neutral hydrophilic end group (e.g., second part 131) is configured to be changed to the third neutral hydrophobic end group (e.g., second part 133) through a third switching mechanism of the switching mechanism, and the third switching mechanism includes flushing the nanopore 205 with a solution containing trimethylsilyl diazomethane via the pump 273.

The fourth neutral and partially charged hydrophobic end group is configured to be changed to a positively charged hydrophilic end group through a fourth switching mechanism of the switching mechanism, where the fourth switching mechanism includes flushing the nanopore with a solution containing dilute hydrochloric acid via the pump 272.

It is contemplated that the organic compound 100 is selected from a group comprising 4-carboxylbenzyl phosphonic acid and 4-aminophenylhydroxamic acid.

The nanopore 205 (and the reservoirs 215 and 220) in the fluidic cell 210 is filled with a solution including at least one of a solvent, an electrolyte, and/or a component, and the solution is chosen from a group of glycerol, polyethylene glycol, water and/or compositions thereof. The electrolyte includes ions of a least one of $Na^+$, $K^+$, $Ca^{2+}$, $Mg^{2+}$, $Cl^-$, $HPO_4^{2-}$, and/or $HCO_3^-$. The component (of the solution) is chosen from a group of ssDNA, dsDNA, and/or custom designed molecules, and the custom designed molecules include and/or contain DNA-components, proteins, polymers, DNA-fragments, and Lambda-DNA.

Further, the nanopore 205 is at least one of a solid state nanopore, a biological nanopore, and/or a planar nanochannel. The voltage source 225 is configured to apply a voltage across the nanopore 205, in which the voltage creates a translocation flow of the third component (e.g., DNA molecule 260) through the nanopore 205, and the nanopore 205 is configured as at least one of a DNA-sequencing device, and/or a molecular filtering device.

Figure 8:
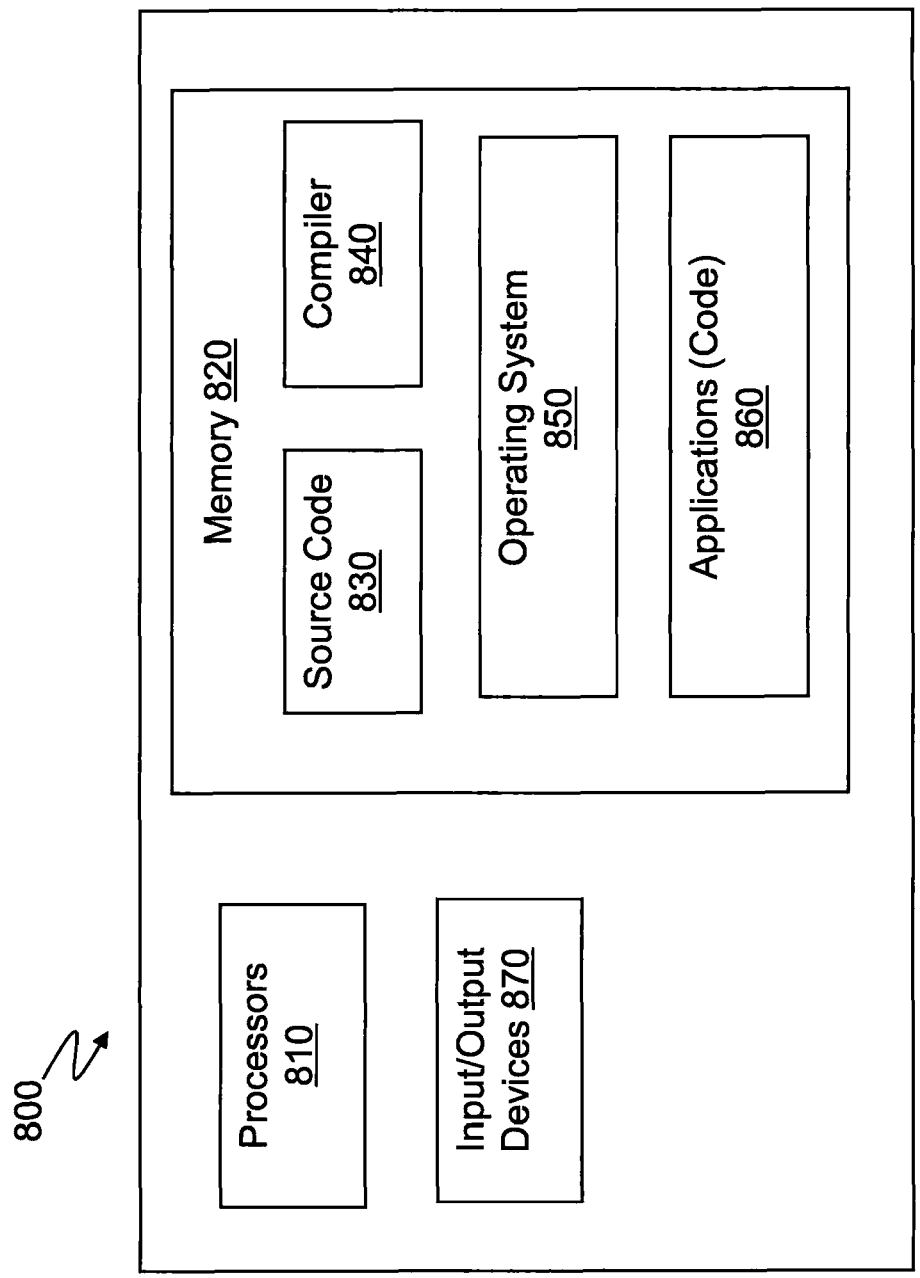
FIG. 8 illustrates an example of a computer having capabilities, which may be included in embodiments.

FIG. 8 illustrates an example of a computer 800 (e.g., as part of the computer setup 255 for testing and analysis) having capabilities, which may be included in exemplary embodiments. Various methods, procedures, modules, flow diagrams, tools, applications, circuits, elements, and techniques discussed herein may also incorporate and/or utilize the capabilities of the computer 800. Moreover, capabilities of the computer 800 may be utilized to implement features of exemplary embodiments discussed herein. One or more of the capabilities of the computer 800 may be utilized to implement, to connect to, and/or to support any element discussed herein (as understood by one skilled in the art) in FIGS. 1-7.

Generally, in terms of hardware architecture, the computer 900 may include one or more processors 810, computer readable storage memory 820, and one or more input and/or output (I/O) devices 870 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 810 is a hardware device for executing software that can be stored in the memory 820. The processor 810 can be virtually any custom made or commercially available processor, a central processing unit (CPU), a data signal processor (DSP), or an auxiliary processor among several processors associated with the computer 800, and the processor 810 may be a semiconductor based microprocessor (in the form of a microchip) or a macroprocessor.

The computer readable memory 820 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 820 may incorporate electronic, magnetic, optical, and/or other types of storage media. Note that the memory 820 can have a distributed architecture, where various components are situated remote from one another, but can be accessed by the processor 810.

The software in the computer readable memory 820 may include one or more separate programs, each of which comprises an ordered listing of executable instructions for implementing logical functions. The software in the memory 820 includes a suitable operating system (O/S) 850, compiler 840, source code 830, and one or more applications 860 of the exemplary embodiments. As illustrated, the application 860 comprises numerous functional components for implementing the features, processes, methods, functions, and operations of the exemplary embodiments. The application 860 of the computer 800 may represent numerous applications, agents, software components, modules, interfaces, controllers, etc., as discussed herein but the application 860 is not meant to be a limitation.

The operating system 850 may control the execution of other computer programs, and provides scheduling, input-output control, file and data management, memory management, and communication control and related services.

The application 860 may be a source program, executable program (object code), script, or any other entity comprising a set of instructions to be performed. When a source program, then the program is usually translated via a compiler (such as the compiler 840), assembler, interpreter, or the like, which may or may not be included within the memory 820, so as to operate properly in connection with the O/S 850. Furthermore, the application 860 can be written as (a) an object oriented programming language, which has classes of data and methods, or (b) a procedure programming language, which has routines, subroutines, and/or functions.

The I/O devices 870 may include input devices (or peripherals) such as, for example but not limited to, a mouse, keyboard, scanner, microphone, camera, etc. Furthermore, the I/O devices 870 may also include output devices (or peripherals), for example but not limited to, a printer, display, etc. Finally, the I/O devices 870 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 870 also include components for communicating over various networks, such as the Internet or an intranet. The I/O devices 870 may be connected to and/or communicate with the processor 810 utilizing Bluetooth connections and cables (via, e.g., Universal Serial Bus (USB) ports, serial ports, parallel ports, FireWire, HDMI (High-Definition Multimedia Interface), etc.).

When the computer 800 is in operation, the processor 810 is configured to execute software stored within the memory 820, to communicate data to and from the memory 820, and to generally control operations of the computer 800 pursuant to the software. The application 860 and the O/S 850 are read, in whole or in part, by the processor 810, perhaps buffered within the processor 810, and then executed.

When the application 860 is implemented in software it should be noted that the application 860 can be stored on virtually any computer readable storage medium for use by or in connection with any computer related system or method. In the context of this document, a computer readable storage medium may be an electronic, magnetic, optical, or other physical device or means that can contain or store a computer program for use by or in connection with a computer related system or method.

The application 860 can be embodied in any computer-readable medium 820 for use by or in connection with an instruction execution system, apparatus, server, or device, such as a computer-based system, processor-containing system, or other system that can fetch the instructions from the instruction execution system, apparatus, or device and execute the instructions. In the context of this document, a "computer-readable storage medium" can be any means that can store, read, write, communicate, or transport the program for use by or in connection with the instruction execution system, apparatus, or device. The computer readable medium can be, for example but not limited to, an electronic, magnetic, optical, or semiconductor system, apparatus, or device.

More specific examples (a nonexhaustive list) of the computer-readable medium 820 would include the following: an electrical connection (electronic) having one or more wires, a portable computer diskette (magnetic or optical), a random access memory (RAM) (electronic), a read-only memory (ROM) (electronic), an erasable programmable read-only memory (EPROM, EEPROM, or Flash memory) (electronic), an optical fiber (optical), and a portable compact disc memory (CDROM, CD R/W) (optical).

In exemplary embodiments, where the application 860 is implemented in hardware, the application 860 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

It is understood that the computer 800 includes non-limiting examples of software and hardware components that may be included in various devices, servers, and systems discussed herein, and it is understood that additional software and hardware components may be included in the various devices and systems discussed in exemplary embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or schematic diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

As described above, embodiments can be embodied in the form of computer-implemented processes and apparatuses for practicing those processes. In embodiments, the invention is embodied in computer program code executed by one or more network elements. Embodiments include a computer program product on a computer usable medium with computer program code logic containing instructions embodied in tangible media as an article of manufacture. Exemplary articles of manufacture for computer usable medium may include floppy diskettes, CD-ROMs, hard drives, universal serial bus (USB) flash drives, or any other computer-readable storage medium, wherein, when the computer program code logic is loaded into and executed by a computer, the computer becomes an apparatus for practicing the invention. Embodiments include computer program code logic, for example, whether stored in a storage medium, loaded into and/or executed by a computer, or transmitted over some transmission medium, such as over electrical wiring or cabling, through fiber optics, or via electromagnetic radiation, wherein, when the computer program code logic is loaded into and executed by a computer, the computer becomes an apparatus for practicing the invention. When implemented on a general-purpose microprocessor, the computer program code logic segments configure the microprocessor to create specific logic circuits.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:
1. A nanodevice, comprising:
  a fluidic cell;
  a membrane dividing the fluidic cell, the membrane comprises SiN;
  a nanopore formed through the membrane, the nanopore being coated with an organic compound, such that the membrane exposed in the nanopore is coated with the organic compound selected from a group comprising 4-carboxylbenzyl phosphonic acid and 4-aminophenylhydroxamic acid;
  a top oxide layer on top of the membrane and a bottom oxide layer on a bottom of the membrane, such that the membrane is exposed in the nanopore in order to be coated with the organic compound;

wherein a first part of the organic compound binds to a surface of the nanopore and a second part of the organic compound is exposed freely inside of the nanopore; and wherein the second part of the organic compound in the nanopore is configured to be switched back and forth among a first surface charge state, a second surface charge state, and a third surface charge state based on a flushing process, the switched back and forth comprising (i) changing the first surface charge state to the second surface charge state through a first flushing process of the flushing process in which the first flushing process comprises flushing the nanopore with a first solution containing 1 M KCl in water at pH 10, (ii) changing the second surface charge state to the first surface charge state through a second flushing process of the flushing process in which the second flushing process comprises flushing the nanopore with a second solution containing hydrochloric acid, (iii) changing the first surface charge state to the third surface charge state through a third flushing process of the flushing process in which the third flushing process comprises flushing the nanopore with a third solution containing trimethylsilyl diazomethane, wherein the first, the second, and the third flushing processes are each performed on the nanopore that is the same nanopore having the second part switched back and forth;

wherein the first, second, and third surface charge states of the organic compound each relate to an inside of the nanopore;

wherein the flushing process occurs in between translocation experiments of a component.

2. The nanodevice of claim 1, wherein, based on the flushing process, the second part of the organic compound is also configured to be switched among a fourth surface charge state in addition to the first surface charge state, the second surface charge state, and the third surface charge state.

3. The nanodevice of claim 2, wherein the fourth surface charge state is configured to be changed through a fourth flushing process of the flushing process; and wherein the fourth flushing process comprises flushing the nanopore with a solution containing hydrochloric acid.

4. The nanodevice of claim 1, wherein the membrane is formed on a wafer and a bottom layer is formed on a bottom part of the wafer;

wherein an oxide is formed on a bottom side of the bottom layer, formed on a side of the bottom layer, formed on a side of the wafer, and formed on a bottom surface of the membrane.

5. The nanodevice of claim 1, wherein the nanopore is a solid state nanopore.

6. The nanodevice of claim 1, wherein the nanopore in the fluidic cell is filled with a solution comprising at least one of a solvent, an electrolyte, and the component.

7. The nanodevice of claim 6, wherein the solution is chosen from a group of glycerol, polyethylene glycol, and compositions thereof.

8. The nanodevice of claim 6, wherein the electrolyte comprises ions of a least one of $Ca^{2+}$, $Mg^{2+}$, $HPO_4^{2-}$, and $HCO_3^-$.

9. The nanodevice of claim 6, wherein the component is chosen from a group of ssDNA, dsDNA, and designed molecules; and wherein the designed molecules include or contain DNA-components, proteins, polymers, DNA-fragments, and Lambda-DNA.

10. The nanodevice of claim 1, further comprising a voltage source configured to apply a voltage across the nanopore, the voltage creating a translocation flow of the component through the nanopore; and wherein the nanopore is configured as at least one of a DNA-sequencing device, and a molecular filtering device.

* * * * *